United States Patent [19]

Kormann et al.

[11] Patent Number: 5,505,880
[45] Date of Patent: *Apr. 9, 1996

[54] MAGNETORHEOLOGICAL FLUID

[75] Inventors: Claudius Kormann, Schifferstadt; Ekkehard Schwab, Neustadt; Martin Laun, Ludwigshafen, all of Germany

[73] Assignee: BASF Aktiengesellschaft, Ludwigshafen, Germany

[*] Notice: The term of this patent shall not extend beyond the expiration date of Pat. No. 5,250,207.

[21] Appl. No.: 341,960

[22] Filed: Nov. 16, 1994

Related U.S. Application Data

[63] Continuation of Ser. No. 948,432, Sep. 23, 1992, abandoned.

[30] Foreign Application Priority Data

Sep. 25, 1991 [DE] Germany .......................... 41 31 846.3

[51] Int. Cl.⁶ .................................. H01F 1/26; H01F 1/44
[52] U.S. Cl. ...................... 252/62.54; 252/62.52; 252/62.56
[58] Field of Search .............................. 252/62.52, 62.54, 252/62.56

[56] References Cited

U.S. PATENT DOCUMENTS

| | | | |
|---|---|---|---|
| 2,661,596 | 12/1953 | Winslow . | |
| 2,751,352 | 6/1956 | Bondi | 252/62.5 |
| 3,228,881 | 1/1966 | Thomas | 252/62.54 |
| 4,329,241 | 5/1982 | Massart . | |
| 4,626,370 | 12/1986 | Wakayama et al. | 252/62.52 |
| 4,810,401 | 3/1989 | Mair et al. | 252/62.56 |
| 4,824,587 | 4/1989 | Kwon et al. | 252/62.56 |
| 4,957,644 | 9/1990 | Price . | |
| 5,143,637 | 9/1992 | Yokouchi et al. | 252/62.52 |
| 5,240,626 | 8/1993 | Thakur et al. | 252/62.54 |
| 5,250,207 | 10/1993 | Kormann et al. | 252/62.54 |

FOREIGN PATENT DOCUMENTS

| | | |
|---|---|---|
| 406692 | 1/1991 | European Pat. Off. . |
| 1306142 | 9/1962 | France . |
| 7918842 | 2/1981 | France . |
| 3-219602 | 9/1991 | Japan . |

OTHER PUBLICATIONS

The Random House College Dictionary, 1973, p. 1022, (Month Unknown).
Chem. Abst. , vol. 87, No. 26, Dec. 26, 1977, Abst. No. 210360q.
Chem. Abst. , vol. 92, No. 12, 1981, Abst. No. 103229k.
Pat. Abst. of Japan, vol. 15, No. 502 (E–1147) Dec. 18, 1991 (abstract in English of JP 32 19 602).
Viscosity of Magnetic Fluid in a Magnetic Field, Rosensweig, Jourl. of Colloid and Interface Science, vol. 29, No. 4, Apr. 1969.
Rheological Characteristics of Magnetic Fluids, JSME International Jourl. vol. 30, No. 263, 1987 (Month Unknown).

*Primary Examiner*—Prince Willis, Jr.
*Assistant Examiner*—Alan D. Diamond
*Attorney, Agent, or Firm*—Keil & Weinkauf

[57] ABSTRACT

A magnetorheological fluid essentially consists of magnetic particles which are coated with a polyelectrolyte and are suspended in a polar liquid. The fluid has a magnetorheological effect of more than 100 Pa, measured in a magnetic field of 100 kA/m.

10 Claims, 2 Drawing Sheets

MAGNETORHEOLOGICAL FLUID

This application is a continuation of application Ser. No. 07/948,432, filed on Sep. 23, 1992 now abandoned.

The present invention relates to a magneto-theological fluid essentially consisting of magnetic particles which are coated with a polyelectrolyte and are suspended in a polar liquid.

Magnetorheological fluids are free-flowing media whose flow properties change rapidly and reversibly under the influence of a magnetic field. The resulting magnetorheological effect corresponds to the increase in shear stress due to a magnetic field, ie. the product of the shear rate and the change in viscosity in the magnetic field.

Fluids of this type are known per se. They are all suspensions of magnetic solids in a liquid with the addition of agents for sedimentation stabilization. Investigations of such media were carried out by, inter alia, R. E. Rosenzweig et al. (J. Colloid and Interface Science, 29 (4) (1969), 680–686). According to these, magnetorheological effects of the order of only 1 Pa were obtained for highly concentrated and dilute hydrocarbon-based magnetic fluids at saturation magnetizations up to 420 Gauβ and shear gradients up to 230 s$^{-1}$ in magnetic fields of up to 1700 kA/m. Investigations into the magnetorheological flow behavior of magnetic fluids based on hydrocarbons, esters and water were also carried out by Kamiyama et al. (JSME International Journal 1987, Vol. 30, No. 263,761–766). These investigations showed that, at shear rates of from 50 to 1,000 s$^{-1}$ and maximum field strengths of 320 kA/m, the magnetorheological effect of hydrocarbon and ester fluids was less than 10 Pa, and a magnetorheological effect of about 30 Pa was obtained in the case of aqueous magnetic fluids, ie. a suspension of magnetic pigments which are stabilized with surfactants. However, magnetic fluids which are kept sediment-stable with the aid of surfactants show a strong tendency to foam. Furthermore, the carrier medium water is extremely problematic owing to its unfavorable corrosion and freezing point properties. This also applies to the aqueous magnetic fluids which are described in FR-A 2 461 521, but without any information on the magnetorheological properties.

These magnetorheological fluids which differ from magnetic fluids, which are used in particular in bearings, rotary transmission leadthroughs and dampers, in their viscosity change in a magnetic field are increasingly being proposed for the construction of clutches and shock absorbers. Such systems are described in, for example, U.S. Pat. No. 2,661,596. Here, mixtures of carbonyl iron pigments, oleic acid and oil are used as media for hydraulic apparatuses. Furthermore, the viscosity in the field-free state is increased by adding soaps. According to U.S. Pat. No. 4,957,644, ferrofluids of carbonyl iron pigments having particle sizes of more than 1 μm in nonpolar organic solvents are used for magnetically controllable clutches. By adding certain low molecular weight complexing agents, it was intended to improve the sedimentation stability, but, because of the rather large magnetic particles, this was not adequately achieved. EP-A 406 692, too, describes a fluid which can be influenced by magnetic fields and comprises carbonyl iron pigments embedded in carbon fibers and present in a carrier oil, without giving more precise information about the magnetorheological effect. In contrast to the stated media generally based on coarse-particled magnetic materials, magnetic fluids having fine, for example superparamagnetic ferrites in hydrocarbons or esters possess low abrasiveness due to the small particle sizes, have short switching times and have an advantageous sedimentation behavior, but the magnetorheological effects required for the transmission of forces are only from 1 to 10 Pa and are too small.

It is an object of the present invention to provide magnetorheological fluids which are distinguished by a high magnetorheological effect and at the same time a low basic viscosity, low abrasiveness, short switching times and good sedimentation stability. It is a further object of the present invention to ensure that this medium does not have a corrosive action and is stable both at high and at low temperatures.

We have found that these objects are achieved by a magnetorheological fluid which essentially consists of magnetic particles which have a particle size of less than 1 μm, are coated with a polyelectrolyte having a molecular weight of from 500 to 250,000 and are suspended in a polar solvent which may additionally contain water and has a boiling point of not less than 100° C., and whose magnetorheological effect is more than 100 Pa, measured in a magnetic field of 100 kA/m.

The novel magnetorheological fluids have a low initial viscosity, which is essential for achieving a high magnetorheological effect. A sort of intermeshing of the coated magnetic particles then takes place in a magnetic field, and the resulting structures offer increased resistance to the flowing medium and the viscosity increases. After the magnetic field has been switched off, the magnetic particles become detached from one another again owing to the electrostatic repulsion, so that the suspension has a low viscosity again.

Both magnetically hard and magnetically soft, isometric and anisometric magnetic particles can be used as magnetic materials for the novel fluids, provided that their mean particle size is less than 1 μm. Of course, mixtures of different magnetic pigments or mixtures of magnetic with nonmagnetic substances may also be used. Preferred classes of substances are superparamagnetic iron oxides, such as $Fe_3O_4$, $\gamma$-$Fe_2O_3$, berthollides and in particular the ferrites described in U.S. Pat. No. 4,810,401 and having the composition $M_vMn_wZn_xFe_yO_z$. Finely divided pigments, as also used for magnetic recording purposes, ie. $\gamma$-$Fe_2O_3$, $CrO_2$, cobalt, pure iron and carbonyl iron pigments, cobalt- and barium-doped ferrites and iron nitrides, are also suitable. The magnetorheological effect generally increases both with the specific saturation magnetization of the materials and with the magnetic field strength. Owing to the fineness of the pigments, the switching process can take place particularly rapidly.

In the novel magnetorheological fluids, these magnetic materials are coated with polyelectrolytes for dispersion and viscosity reduction. Polyelectrolytes result in an increase in the surface charge of the solid particles. The pH, which influences the rheological properties of the suspension, is important here. By varying the pH, the charge carrier concentration in the polyelectrolytes can be adjusted in a suitable manner. When anionic polyelectrolytes are used, it has proven advantageous if the pH is greater than their acid constant (pKa), whereas in the case of cationic polyelectrolytes the pH is preferably smaller than the pKa. Furthermore, the flow properties can be advantageously influenced by adjusting the ionic strength. A large number of polyelectrolytes having a molecular weight of from 500 to 250,000 are suitable. These polymers preferably have from 5 to 1,000 charges in the molecular skeleton. Polyelectrolytes selected from the group consisting of polyacrylate, acrylic acid/acrylamide copolymers, modified polyacrylates, phosphonomethylated polycarboxylates, polyvinylphosphonic acids, polyvinylphosphoric acids, polyamines, polyvinylamines polysulfonic acids and polyphosphoric acids are particularly suitable. In the case of the polyacrylates, a pH of from 4 to 12 has proven particularly advantageous. In addition to the stated polyelectrolytes, it is also possible to use further ligands which increase the surface charge.

The carrier media present in the novel magnetorheological fluids are polar solvents which have at least low solubility for water. These are alcohols, ethers and esters as well as mixtures thereof. While anhydrous magnetorheological fluids can be prepared by completely stripping off the water under reduced pressure, a low water content improves the dispersing and flow properties of the magnetic fluid. Advantageously, the water content of the final composition should not exceed 20% by weight. Examples of suitable polar liquids are alcohols and ethers, such as diethylene glycol methyl ether, diethylene glycol mono- and diethyl ether or diethylene glycol monomethyl ether, $C_2$–$C_6$-alkyl esters of $C_1$–$C_6$-alkanemonocarboxylic acids, such as hexyl acetate, cyclohexyl acetate, pentyl propionate, ethyl butyrate, methyl pentanecarboxylate, ethyl pentanecarboxylate or methyl hexanecarboxylate, or $C_1$–$C_6$-dialkyl esters of $C_1$–$C_7$-alkanedicarboxylic acids, such as dihexyl malonate, dihexyl succinate, dipentyl glutarate, di-n-butyl adipate, di-n-butyl pimelate, di-n-propyl hexanedicarboxylate or diethyl azelaate. Ethylene glycol, diethylene glycol, glycerol, polyethylene glycol and oligo- (eg. tetra-)methylene glycol dimethyl ether are particularly suitable.

The composition of the magnetorheological fluid is variable within certain limits. Thus, the solids content is preferably from 10 to 80, in particular from 20 to 60, % by weight.

Novel magnetorheological fluids having this composition have unlimited flow owing to the extremely small tendency to sedimentation, which, for example, is less than 10% after storage for 1 week, so that they are very useful for hydraulic apparatuses, for example for shock absorbers. Because of the substantially anhydrous carrier medium, advantageous corrosion properties and low temperature resistance are achieved. Other important features are that they have viscosities of less than 10 Pas at shear rates of 10 $s^{-1}$ and give magnetorheological effects of more than 100 Pa, preferably up to 10,000 Pa, in a magnetic field of 100 kA/m. The Examples which follow illustrate the invention.

The BET surface measured in the Examples below was determined according to DIN 66,132 by means of a Ströhlein areameter from Ströhlein Düsseldorf, by the one-point difference method according to Haul and Dümbgen.

The sedimentation behavior was measured using a height-resolving susceptibility meter, and the monotonic distribution of the magnetic substance was determined.

Figure 1A:
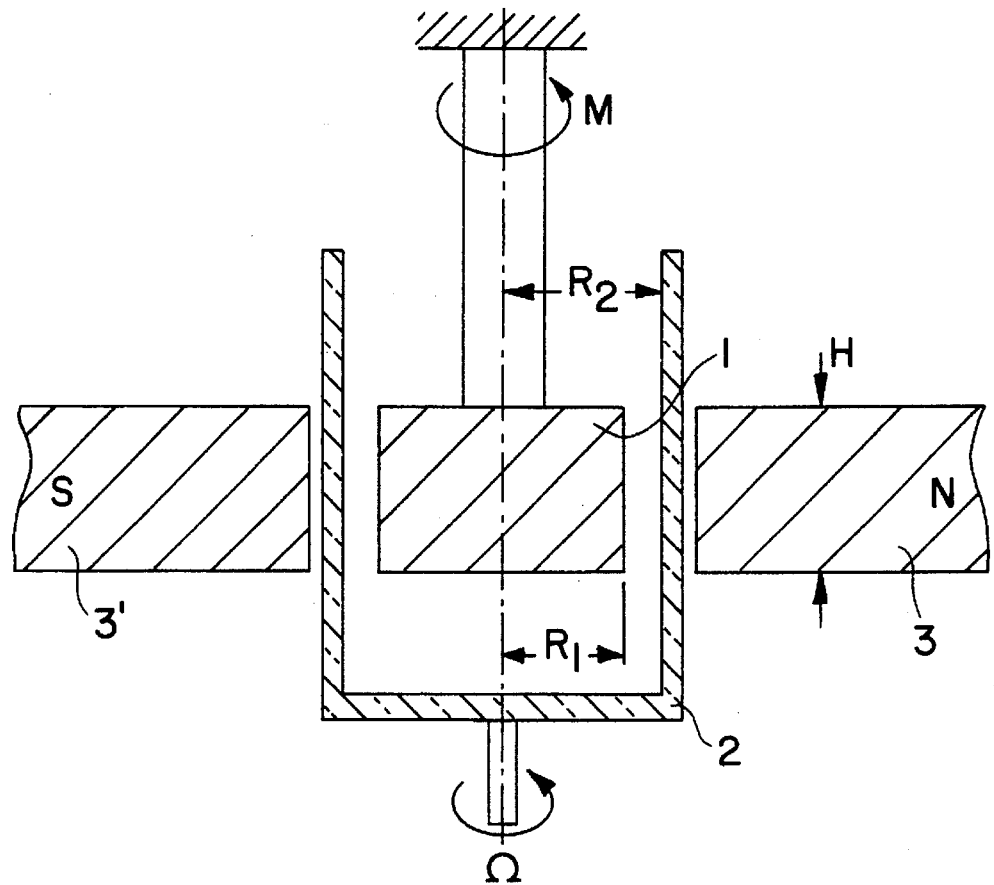
FIGS. 1a and 1b show a Couette rheometer with a superimposed magnetic field.

The magnetorheological effect was measured using a Couette rheometer CRM with a superposed magnetic field of 100 kA/m at room temperature. The Couette measuring arrangement used, having a superposed magnetic field, is shown in FIGS. 1a (side view) and 1b (plan view). There, the sample is present in the gap between a cylindrical, stationary iron stator 1 having a radius $R_1$ and a polyamide cup 2 which rotates at an angular speed $\Omega$ and has an internal radius $R_2$. The torque M acting on the stator is measured. If H is the height of the stator, the wall shear stress $\tau$ at the stator in the field-free case is $$\tau = \frac{M}{2\pi R_1^2 H}$$

$$\dot{\gamma} = \frac{\Omega}{1 - (R_1/R_2)^2}$$

Figure 1B:
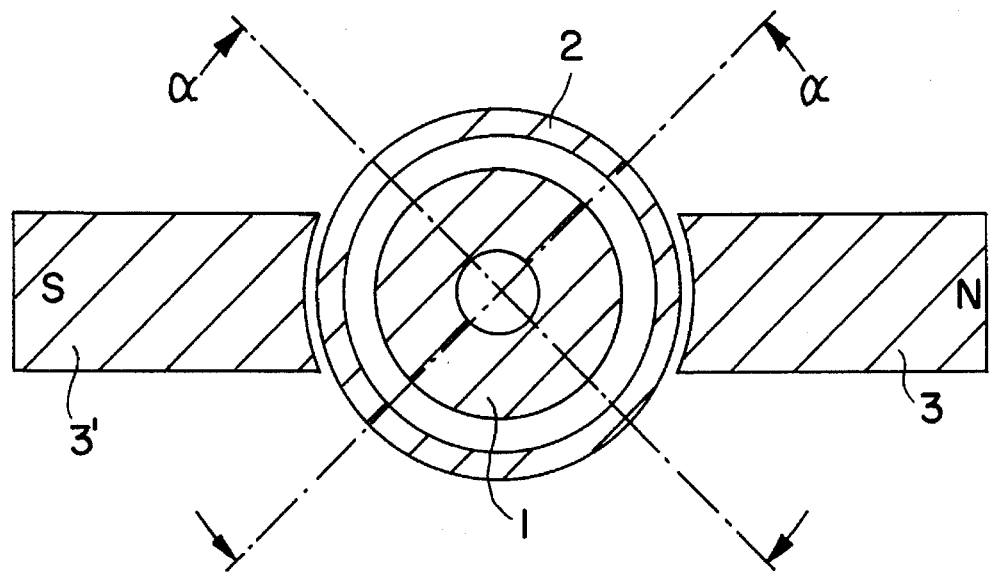

Due to the geometry of the pole pieces 3 and 3', only parts of the sample are within the two sectors with the angle $\alpha$ (in radians) in the magnetic field. If the shear stress measured at constant shear rate increases, under the influence of a magnetic field at right angles to the shear plane, from the field-free value $\tau$ to the value $\tau_M = \tau + \Delta\tau_M$, with the geometry shown in FIG. 1 this leads to an increase in the torque from M to $M_M$:

$$M_M/M = 1 + (\alpha/\pi)(\Delta\tau_M/\tau)$$

The magnetorheological effect is obtained from the torque ratio as $$\Delta\tau_M/\tau = (M_M/M - 1)/(\alpha/\pi)$$

The magnetorheological effect was measured in a field of 100 kA/m in the gap between pole pieces and stator.

EXAMPLE 1

A solution of 1084.6 g of iron(III) chloride hexahydrate, 139.9 g of manganese(II) chloride tetrahydrate and 375.4 g of iron(II) chloride dihydrate in 1200 ml of water was added dropwise at 30° C. to a solution of 689.2 g of sodium hydroxide and 38.4 g of zinc oxide in 690 ml of water in the course of 1 hour.

After precipitation was complete, a pH of 10.8 was measured. The mixture was heated to 70° C. kept at this temperature for 1 hour and cooled to room temperature, after which the pH was brought to 9. The resulting ferrite suspension was filtered and washed chloride-free. The manganese zinc ferrite ($Mn_{0.3}Zn_{0.2}Fe_{2.5}O_4$) obtained in this manner has the following characteristics after drying at 80° C.: specific surface area $SN_2 = 97$ m$^2$/g, magnetization $M_m/\rho = 76$ nTm$^3$/g.

335 g of ethylene glycol were added to 940 g of this filter cake, which contained 435 g of ferrite and 505 g of water. The water was stripped off down to a small residual amount (about 40 g) in a rotary evaporator at 65° C. under reduced pressure. A mixture of 59 g of the sodium salt of a polyacrylic acid having a molecular weight of 4,000 and 72 ml of water was added. The suspension was then dispersed for 20 minutes under the action of high shear forces, using an Ultra Turrax disperser. After storage for 3 days, decanting was carried out. Finally, 720 g of suspension having the following composition were obtained: 45% by weight of ferrite, 7% by weight of polyacrylate, 12% by weight of water and 36% by weight of ethylene glycol. The pH was 11.9. The sedimentation behavior was characterized after 1 week using a localizing susceptibility meter: the concentration of the magnetic pigment was about 7% higher at the bottom of a 10 cm high fluid column than at the upper end.

The magnetorheological effect in the shear rate range from 7 to 700 $s^{-1}$ was 100–110 Pa. The viscosity at a shear gradient of 10 $s^{-1}$ was 3 Pas.

EXAMPLE 2

A solution of 9.25 kg of iron(III) chloride, 5.25 kg of iron(II) chloride dihydrate, 0.9 kg of zinc chloride and 2.0 kg of manganese(II) chloride tetrahydrate in 25 l of water, with the addition of 50 ml of concentrated HCl, was added dropwise at ±26° C. to a solution of 10.2 kg of sodium hydroxide in 38 l of water in the course of 1 hour.

After precipitation was complete, a pH of 10.4 was measured. The mixture was heated to 70° C., kept at this temperature for 1 hour and cooled to room temperature, after which the pH was brought to 9. The resulting ferrite suspension was filtered and washed chloride-free. The manganese zinc ferrite ($Mn_{0.3}Zn_{0.2}Fe_{2.5}O_4$) obtained in this manner has the following characteristics after drying at 80° C.: specific surface area $SN_2=93$ m$^2$/g, magnetization $M_g/\rho=79$ nTm$^3$/g.

397 g of the filter cake obtained as described above, which contained 100 g of ferrite and 297 g of water, was stirred with a mixture of 20 g of the sodium salt of a polyacrylic acid having a molecular weight of 4,000 and 24 g of water. 100 g of ethylene glycol were added, and the suspension was dispersed for 1 hour under the action of high shear forces using an Ultra Turrax disperser.

The water was then stripped off in a rotary evaporator at 65° C. under reduced pressure from a water pump. Finally, 221 g of suspension having the following composition were obtained: 47% by weight of ferrite, 7% by weight of polyacrylate, 1% by weight of water and 45% by weight of ethylene glycol. The pH was about 10.7.

The sedimentation behavior was characterized after 1 week using a height-resolving susceptibility meter: the concentration of the magnetic pigment at the bottom of a 10 cm high column was just as high as at the upper edge. The magnetorheological effect in a field of 100 kA/m was 330 Pa. The viscosity at a shear gradient of 25 s$^{-1}$ was 4 Pas.

COMPARATIVE EXPERIMENT 1

20 g of oleic acid and 80 g of a nonpolar oil were added to 100 g of carbonyl iron pigment having a mean particle size of from 2 to 4 μm, and dispersing was carried out for 10 minutes under the action of high shear forces, using the apparatus described in Example 2. The resulting suspension was unsuitable as a magnetorheological fluid since it exhibited strong sedimentation: after only 1 hour, a compact non-free-flowing sediment had formed, covered with a layer of clear oil.

COMPARATIVE EXPERIMENT 2

30 g of tributyl phosphate, 10 g of Na$_2$EDTA and 50 g of a nonpolar oil were added to 150 g of carbonyl iron pigment having a mean particle size of from 2 to 4 μm, and homogenization was carried out on a roller stand for 15 hours.

This suspension too was unsuitable since it exhibited a strong tendency to sedimentation. After storage for only 1 day, a 10 cm high column had separated into a compact 5 cm sediment and a pigment-free oil layer of the same height.

EXAMPLE 3

10 g of a 45% strength by weight solution of the sodium salt of a polyacrylic acid having a molecular weight of 4,000, 90 g of ethylene glycol and 150 g of water were added to 50 g of a commercial pure iron pigment having a BET surface area of 53 m$^2$/g ($Mm/\rho=145$ nTm$^3$/g, $Mr/\rho=70$ nTm$^3$/g). The mixture was dispersed for 15 minutes under the action of high shear forces. The water was then stripped off at 65° C. in a rotary evaportor under reduced pressure from a water pump. Finally, 151 g of suspension having the following composition were obtained: 33% by weight of metal pigment, 3% by weight of polyacrylate, about 4% by weight of water and 60% by weight of ethylene glycol. The magnetorheological effect in a field of 100 kA/m was 1,000 Pa. The viscosity at a shear gradient of 25 s$^{-1}$ was 6 Pas.

EXAMPLE 4

The magnetorheological fluids described below were prepared by a standard method. The pigment properties (BET, Mm/ρ) and the ratios of pigment, dispersant and solvent were chosen according to the table. The pigment (100 g in each case) was used in the form of a moist filter cake or was made into a paste with water (solids content 20–35% by weight). It was then mixed with an aqueous (about 10–50% strength by weight) solution of the dispersant and with the amount of solvent, triethylene glycol, shown in the table. The dispersant was obtained by neutralizing the acidic form of the polyelectrolyte with NaOH or LiOH to a pH of 9–11. The amount of dispersant shown in the table relates to the solids content including the cations. The pH measurement and, if necessary, the pH correction to the pH shown in the table were carried out after the dispersing step. The dispersing step comprised treatment of the mixture with an Ultra Turrax disperser for 1 hour. Drying of the dispersed mixture, a process which took from about 4 to 21 hours and was monitored via the weight decrease, was finally carried out in a rotary evaporator at 120°–140° C. at atmospheric pressure and then at reduced pressure. The saturation magnetization Ms [Gauss] was measured for the dry fluid. It can be calculated as follows: Ms=10× density×Mm/ρ. Before the measurement of the magnetorheological properties, the samples were subjected to shearing: the samples were introduced into a mixing container at 80° C. and were cooled to 25° C. with shearing (700 Pa shearing stress). The viscosity was then measured (without a field) at a shear rate of γ=26 s$^{-1}$. After a magnetic field of 160 kA/m had been switched on, the magnetorheological effect was measured at the same shear rate.

TABLE

| Pigment: | BET m$^2$/g | Mm/ρ nTm$^3$/g | Dispersant (molecular weight) | Solvent | pH | Ms [G] | MR effect [Pa] | Viscosity [Pas] |
|---|---|---|---|---|---|---|---|---|
| 100 g of MnZn ferrite | 67 | 81 | 5 g Na—PA§ (MW 4000) | 130 g triethylene glycol | 10 | 560 | 400 | 2.5 |
| 100 g of MnZn ferrite | 88 | 79 | 15 g Na—PA (MW 1200) | 120 g triethylene glycol | 9.7 | 610 | 600 | 3 |
| 100 g of MnZn ferrite | 88 | 79 | 15 g Li—PA (MW 4000) | 150 g triethylene glycol | 9.8 | 520 | 1000 | 5.5 |
| 100 g of | 56 | 83 | 15 g Na—PA (MW 4000) | 135 g triethylene | 9 | 560 | 1300 | 4.2 |

TABLE-continued

| Pigment: | BET m²/g | Mm/ρ nTm³/g | Dispersant (molecular weight) | Solvent | pH | Ms [G] | MR effect [Pa] | Viscosity [Pas] |
|---|---|---|---|---|---|---|---|---|
| precipitated magnetite | | | | glycol | | | | |
| 95 g of MnZn ferrite | 51 | 84 | 15 g Na—PA (MW 4000) | 135 g triethylene glycol | 10 | 560 | 850 | 4.5 |
| 5 g of acicular $Fe_3O_4$ | 17 | 103 | | | | | | |
| 95 g of MnZn ferrite | 51 | 84 | 15 g Na—PA (MW 4000) | 135 g triethylene glycol | 10 | 510 | 1100 | 4.5 |
| 5 g of goethite | 69 | — | | | | | | |

§PA = polyacrylate

EXAMPLE 5

Figure 2:
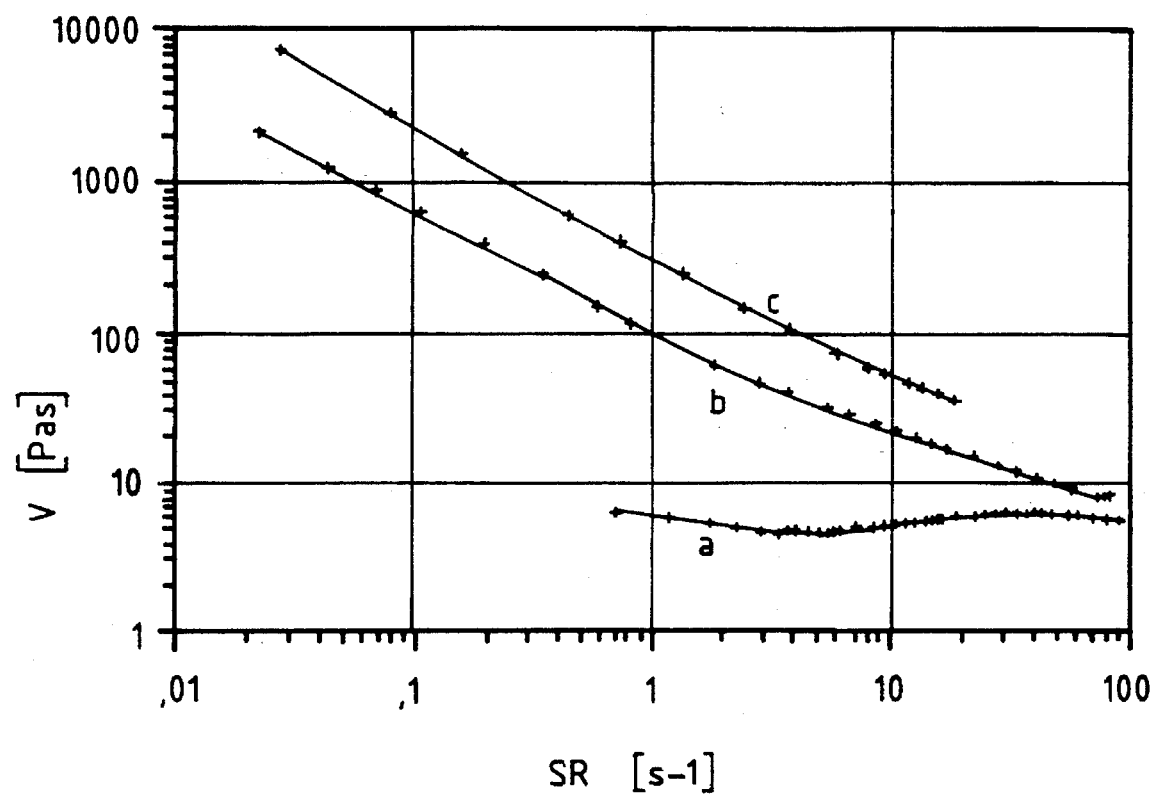
FIG. 2 shows a plot of viscosity as a function of shear rate for a magnetorheological fluid.

A filter cake of 500 g of MnZn ferrite which had BET=51 m²/g and Mm/ρ=84 nTm³/g and 1250 g of water was homogenized with a solution of 75 g of the potassium salt of polyacrylic acid having a molecular weight of 4000 in the course of one and a half hours using a Kotthoff mixing apparatus under nitrogen, and was kept at pH 10 by adding 14 g of NaOH (50% strength by weight). After the addition of 675 g of triethylene glycol, dispersing was continued for a, further 20 minutes. A pH of 9.7 was measured. Half this mixture was dried in a rotary evaporator: initially for 5 hours at 120° C. under atmospheric pressure and then for 13 hours at 70° C. and reduced pressure, and the sample was finally stirred in a laboratory stirrer for a further 5 hours at room temperature. 627 g of magnetorheological fluid were obtained. Before the measurement, the sample was introduced into a measuring container at 80° C. and was cooled to 25° C. with shearing (about 700 Pa shearing stress). The viscosity V at 25° C. as a function of the shear rate SR and of the applied magnetic field strength is shown in FIG. 2, where curve a was measured without magnetic field, curve b in a magnetic field of 80 kA/m and curve c in a field of 160 kA/m.

COMPARATIVE EXPERIMENT 3

A magnetic fluid, prepared by a method based on Example 28 of U.S. Pat. No. 4,810,401, i.e. with the use of a low molecular weight surfactant in an ester oil, is characterized as follows: saturation magnetization: 900 Gauss, viscosity without magnetic field at a shear rate of $\gamma=18$ s⁻: $\eta°=2.0$ Pas. The magnetorheological effect of this fluid (measured at $\gamma=18$ s⁻¹) in a magnetic field having a strength of 128 kA/m was less than 2 Pa.

We claim:

1. A composition consisting essentially of a magnetorheological fluid, wherein magnetic particles having a particle size of less than 1 μm are coated with a polyelectrolyte having a molecular weight of from 500 to 250,000 selected from the group consisting of phosphonomethylated polycarboxylates, polyvinylphosphonic acids, polyvinylphosphoric acids, polyamines, polyvinylamines, polysulfonic acids and polyphosphoric acids, and are suspended in a polar solvent having a boiling point of not less than 100° C., wherein said composition contains up to 20% by weight of water, and the magnetorheological effect is more than 100 Pa and up to 10,000 Pa, measured in a magnetic field of 100 kA/m.

2. The composition as defined in claim 1, wherein the polar solvent is selected from the group consisting of alcohols, ethers and esters.

3. The composition as defined in claim 1, wherein the magnetic particles in the fluid are electrostatically stabilized against sedimentation.

4. The composition as defined in claim 1, wherein its viscosity is less than 10 Pas, measured at a shear gradient of 25 s⁻¹ at room temperature.

5. The composition as defined in claim 1, wherein sedimentation of the magnetorheological fluid after storage for one week is less than 10%.

6. A magnetorheological fluid, wherein magnetic particles having a particle size of less than 1 μm are coated with a polyelectrolyte having a molecular weight of from 500 to 250,000 selected from the group consisting of phosphonomethylated polycarboxylates, polyvinylphosphonic acids, polyvinylphosphoric acids, polyamines, polyvinylamines, polysulfonic acids and polyphosphoric acids, and are suspended in a mixture of water and one polar solvent which has a boiling point of not less than 100° C., and the magnetorheological effect is more than 100 Pa and up to 10,000 Pa, measured in a magnetic filed of 100 kA/m, and the water content does not exceed 20% by weight.

7. A magnetorheological fluid as defined in claim 6, wherein the polar solvent is selected from the group consisting of alcohols, ethers and esters.

8. A magnetorheological fluid as defined in claim 6, wherein the magnetic particles in the fluid are electrostatically stabilized against sedimentation.

9. A magnetorheological fluid as defined claim 6, wherein its viscosity is less than 10 Pas, measures at a shear gradient of 25 s⁻¹ at room temperature.

10. A magnetorheological fluid as defined in claim 6, wherein sedimentation after storage for one week is less than 10%.

* * * * *

UNITED STATES PATENT AND TRADEMARK OFFICE
CERTIFICATE OF CORRECTION

PATENT NO. : 5,505,880
DATED : Apr. 9, 1996
INVENTOR(S) : Kormann, et al

It is certified that error appears in the above-indentified patent and that said Letters Patent is hereby corrected as shown below:

Column 8, claim 6, line 44, "filed" should be --field--.

Column 8, claim 9, line 52, "measures" should be --measured--.

Signed and Sealed this

Tenth Day of September, 1996

Attest:

BRUCE LEHMAN

Attesting Officer        Commissioner of Patents and Trademarks